(12) United States Patent
Fargahi et al.

(10) Patent No.: US 11,740,144 B2
(45) Date of Patent: Aug. 29, 2023

(54) STRAIN SENSOR ARRANGEMENT AND METHOD OF PRODUCING SAME

(71) Applicant: BIOTRONIK AG, Buelach (CH)

(72) Inventors: Amir Fargahi, Buelach (CH); Carina Haber, Singen (DE); Matthias Wesselmann, Ruedlingen (DE); Jeremy Wernli, Wettingen (CH)

(73) Assignee: BIOTRONIK AG, Buelach (CH)

( * ) Notice: Subject to any disclaimer, the term of this patent is extended or adjusted under 35 U.S.C. 154(b) by 700 days.

(21) Appl. No.: 16/778,493

(22) Filed: Jan. 31, 2020

(65) Prior Publication Data

US 2020/0249105 A1 Aug. 6, 2020

(30) Foreign Application Priority Data

Feb. 6, 2019 (EP) .................................. 19155736

(51) Int. Cl.
*G01L 1/22* (2006.01)
*A61F 2/958* (2013.01)
*A61M 25/10* (2013.01)

(52) U.S. Cl.
CPC ............ *G01L 1/2287* (2013.01); *A61F 2/958* (2013.01); *A61M 25/10187* (2013.01); *A61M 2025/1031* (2013.01); *A61M 2205/332* (2013.01); *A61M 2205/3317* (2013.01)

(58) Field of Classification Search
CPC .... A61M 25/10187; A61M 2025/1031; G01L 1/2287; A61B 2018/0022
See application file for complete search history.

(56) References Cited

U.S. PATENT DOCUMENTS

| 2010/0087782 A1* | 4/2010 | Ghaffari ............. A61B 5/02007 623/1.11 |
| 2014/0331741 A1* | 11/2014 | Shah ................... G01P 15/0891 73/12.06 |
| 2017/0226362 A1 | 8/2017 | Fratello et al. |
| 2018/0079924 A1* | 3/2018 | Lai ......................... H01Q 1/368 |
| 2018/0149531 A1 | 5/2018 | Atashbar et al. |
| 2019/0023929 A1* | 1/2019 | Lanceros Mendez .... G01L 1/18 |

FOREIGN PATENT DOCUMENTS

WO    20180228407 A1    12/2018

OTHER PUBLICATIONS

Bessonov, A. A., and M. N. Kirikova. "Flexible and Printable Sensors." Nanotechnologies in Russia, vol. 10, No. 3-4, 2015, pp. 165-180., doi:10.1134/s1995078015020044.
Schmitz, Volker, EP Search Report for Application No. 19155736.2 dated Aug. 6, 2019.

* cited by examiner

*Primary Examiner* — Tasnim Mehjabin Ahmed
(74) *Attorney, Agent, or Firm* — Greer, Burns & Crain, Ltd.; Steven P. Fallon

(57) ABSTRACT

An arrangement of an expandable substrate and a strain sensor applied onto a surface of the substrate. The strain sensor is made from an ink composition that is a mixture of a conductive silver ink and a conductive carbon ink. A ratio between the conductive silver ink and the conductive carbon ink lies in a range between 30:70 and 70:30 in on arrangement and between 40:60 and 60:40 in another. A method for forming the arrangement directly prints the strain sensor on the substrate.

14 Claims, 4 Drawing Sheets

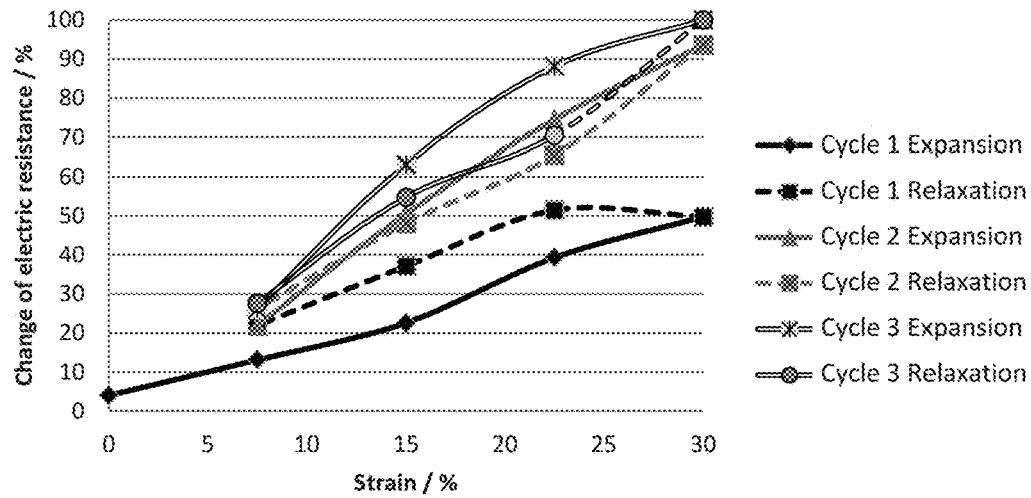
FIG 5 (comparative example)
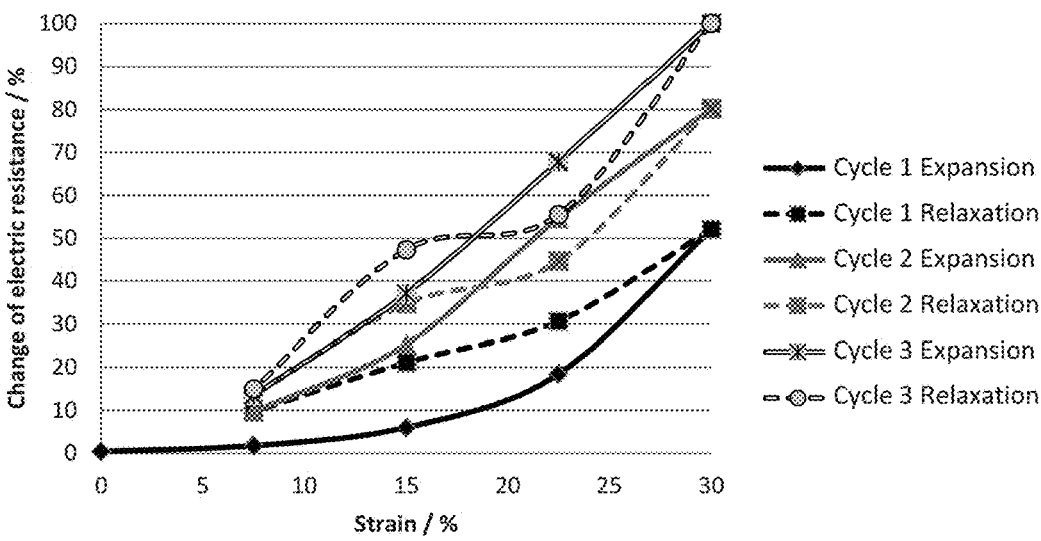
FIG 6 (comparative example)

STRAIN SENSOR ARRANGEMENT AND METHOD OF PRODUCING SAME

PRIORITY CLAIM

This application claims priority under 35 U.S.C. § 119 and all applicable statutes and treaties from prior European Application EP 19155736.2, filed Feb. 6, 2019.

FIELD OF THE INVENTION

A field of the invention is strain sensor devices for elastic and expansible substrates. Another field of the invention is expansible implant devices with strain sensors, such as balloon catheters.

BACKGROUND

Strain sensors are often applied to an outer surface of a balloon catheter to measure the strain or expansion of the balloon catheter. The accuracy of such measurements strongly depends on the physical properties of the material used for forming the strain sensor. When measuring the strain of a balloon catheter, hysteresis can be observed between measurements performed upon expansion of the balloon catheter and measurements performed upon relaxation of the balloon catheter. Known strain sensors affected by hysteresis show a delayed response to a change in strain depending on the mode of action applied (expansion or relaxation). This results in inaccurate measurements such that the exact stage of expansion of a balloon catheter cannot be properly determined.

This inaccuracy can have a severe medical impact. Typically, a balloon catheter is inserted into the vascular system of a human or animal in order to expand a vascular wall in a constricted area. The balloon catheter may be used, e.g., for expanding a stent that is used to stabilize the vascular walls at a previously constricted area so as to keep a sufficiently big diameter for blood flow. Such a stent is—like the vascular wall itself—an elastic system that recoils after expansion. Thus, typically a 10 to 15% over-expansion is necessary in order to achieve the desired expansion of the stent and the vascular wall. Thereby, the expansion of the stent is performed with a balloon catheter. If the stent is not sufficiently over-expanded, the stent might not be in sufficiently close contact with the vascular wall so that the endothelium of the vascular wall cannot grow over the stent. In such a case, turbulences of the blood flow can occur at the struts of the stent leading to local thrombosis. In less severe cases of insufficient over-expansion of the stent, the stent might be in contact with the vascular wall and can grow into the vascular wall. However, even then there might be a higher probability that in case of a high blood pressure the vascular wall is inflated and pressed away from the stent. In such a case, a freshly grown endothelium layer may rupture. Periodic incidents of stent ingrowth and rupture of a freshly grown endothelium layer have been reported that lead to a cascade of irritations, inflammations and finally a restenosis.

If a stent is expanded too much, the vessel in which the stent is inserted can rupture. This results in even more severe medical consequences.

Strain sensors may also be used on other types of substrates and in other medical and non-medical technical fields, e.g., on wearable computers and in the automotive industry.

WO 2015/196169 A1 describes a medical device comprising a printed ablation electrode disposed on an outer surface of a balloon catheter. Thereby, a metallic ink such as silver ink may be used to manufacture the ablation electrode.

WO 2013/017697 A1 describes a substrate with a working electrode comprising three parts. The first part is made from a conductive carbon material, the second part is made from a conductive silver material, and the third part of the electrode is made from a mixture of the conductive carbon material and the conductive silver material. This mixture of conductive silver material and conductive carbon material is used to reduce silver contaminations in electrochemical cells.

There is a medical need to provide strain sensors on balloon catheters used for expanding a stent to measure the strain of the balloon and therewith the strain of corresponding stent with high accuracy to guarantee that the stent is over-expanded by the desired percentage, such as 10 to 15%, resulting in an optimum implantation of the stent.

SUMMARY OF THE INVENTION

A preferred embodiment is an arrangement of an expandable substrate and a strain sensor applied onto the surface of the substrate. The strain sensor is made from an ink composition comprising a mixture of a conductive (and stretchable) silver ink and a conductive (and stretchable) carbon ink. A ratio between the conductive silver ink and the conductive carbon ink lies in a range between 30:70 and 70:30 by volume.

BRIEF DESCRIPTION OF THE DRAWINGS

Further details of aspects of the present invention will be described in the following with respect to exemplary embodiments and accompanying Figures. In the Figures:

FIG. 5 shows a diagram on the change of the electric resistance of a third hybrid ink in dependence on the applied strain;

FIG. 6 shows a diagram on the change of the electric resistance of a fourth hybrid ink in dependence on the applied strain.

DETAILED DESCRIPTION OF THE PREFERRED EMBODIMENTS

Figure 1:
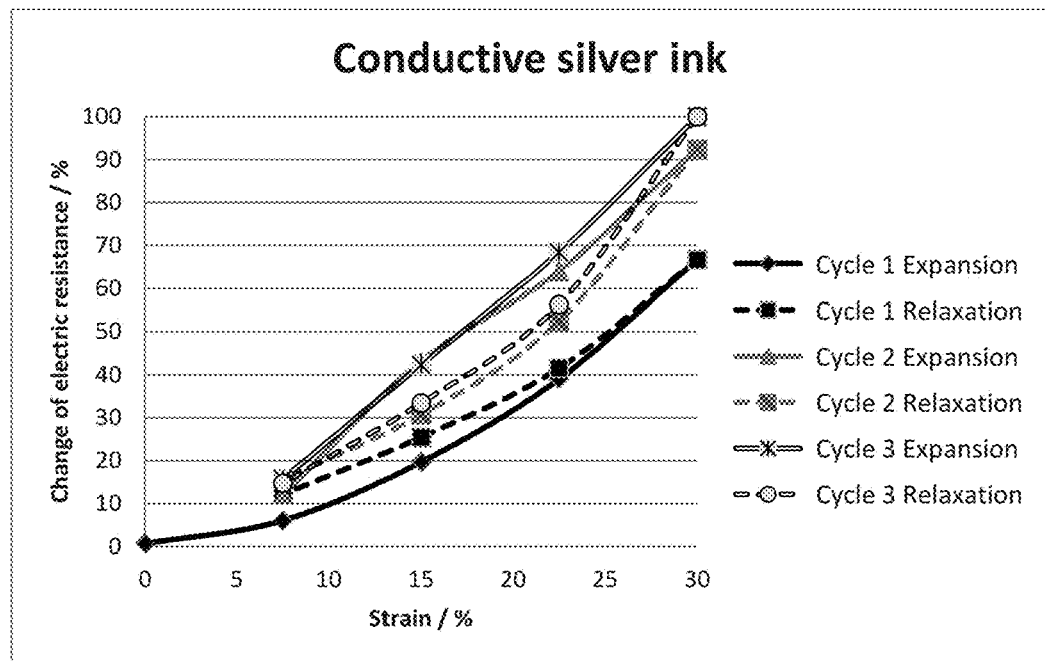
FIG. 1 shows a diagram on the change of the electric resistance of conductive silver ink in dependence on the applied strain.

Unless otherwise indicated, all ratios in the following description are volume ratios. Thus, preferred ratios between the conductive silver ink and the conductive carbon ink lie in a range between 30:70 and 70:30 by volume.

Preferred arrangements include a strain sensor of a hybrid ink including conductive silver ink and conductive carbon ink in the ratios that provide superior effects with respect to pure conductive silver ink, pure conductive carbon ink and hybrid inks including both conductive silver ink and conductive carbon ink in other ratios. Strain sensors made from pure conductive silver ink and strain sensors made from pure conductive carbon ink show a significant hysteresis, i.e., a different behavior upon expansion and upon relaxation. Thus, measurement obtained upon expansion and obtained upon relaxation of such strain sensors or the substrates onto which the strain sensors are applied, cannot be well compared. The same is true for hybrid inks including conductive silver ink and conductive carbon ink in a ratio of 75:25 or in a ratio of 25:75. Surprisingly, strain sensors made from a hybrid ink of the invention with conductive silver ink and conductive carbon ink in a ratio between 30:70 and 70:30 by volume show a reduced hysteresis compared to inks including only conductive silver ink or conduction carbon ink. Strain sensors made from a hybrid ink including conductive silver ink and conductive carbon ink in a ratio between 40:60 and 60:40 show a significantly reduced hysteresis so that the overall accuracy of such strain sensors is much higher than that of strain sensors made from pure conductive silver ink, pure conductive carbon ink or other hybrid inks.

It is surprising that the electric properties of hybrid inks including conductive silver ink and conductive carbon ink in a ratio between 30:70 and 70:30 show a different behavior than either hybrid inks having a higher conductive silver ink portion or hybrid inks having a higher conductive carbon ink portion. Surprisingly, there exists a comparatively narrow window of ratios between conductive silver ink and conductive carbon ink in which the corresponding hybrid ink has electric properties that can well be exploited for manufacturing highly accurate strain sensors or at least strain sensors having higher accuracy than strain sensors as known in the prior art. In a preferred embodiment, the ink composition of the strain sensor consists of conductive silver ink and conductive carbon ink having a ratio that lies in a range between 30:70 and 70:30 by volume In an embodiment, the ratio between the conductive silver ink and the conductive carbon ink lies in a range between 40:60 and 60:40.

In a more preferred embodiment, the ratio between the conductive silver ink and the conductive carbon ink lies in a range between 45:55 and 55:45, in particular between 47:53 and 53:47, in particular between 48:52 and 52:48, in particular at 50:50. Thereby, a ratio of 50:50 encompasses also values plus minus one, i.e., ratios lying in a range between 51:49 and 49:51.

Generally, all commercially available conductive (and stretchable) silver inks and conductive (and stretchable) carbon inks can be used for manufacturing the strain sensor. In an embodiment, the ink composition has a solids content between 40% and 55% determined at 150° C. Such a solids content is particularly appropriate for using the inks in order to manufacture a strain sensor.

In an embodiment, the strain sensor has a thickness lying in a range between 1 and 200 µm, in particular between 5 and 100 µm, in particular between 10 and 190 µm, in particular between 20 and 180 µm, in particular between 30 and 170 µm, in particular between 40 and 160 µm, in particular between 50 and 150 µm, in particular between 60 and 140 µm, in particular between 70 and 130 µm, in particular between 80 and 120 µm, in particular between 90 and 110 µm, in particular around 100 µm. In a preferred embodiment where the expandable substrate is a balloon of a balloon catheter, the strain sensor has a thickness lying in a range between 1 and 10 µm, in particular between 3 and 7 µm, in particular around 5 µm.

The substrate can be generally made from any appropriate material that is expandable or elastic. Polymeric materials are particularly appropriate. Suitable polymerich materials could be polyethylenterephthalate (PET), polyetheretherketon (PEEK), polyetherblockamide (Pebax), polyamide (PA), polyurethane, polydimethylsiloxane (PDMS), polyvinylalcohole (PVA), polycarbonate (PC), parylene, parylene C, biodegradable polymers as Ecoflex®, polystyrene, silicon rubber, polyethersulfone (PES), polyimide (PI), polymethylmethacrylate (PMMA), polyvinylchloride (PVC), fabrics, papers or polymer based fabrics.

In a preferred embodiment where the expandable substrate is a balloon of a balloon catheter, the substrate is made of polyamide as PA6, PA11 or PA12.

The substrate can have a thickness between several micrometers up to several millimeters such as, e.g., any thickness between 1 µm and 20 mm.

In an embodiment, the substrate is a wearable computer or part of such a wearable computer. Wearable computers, also simply referred to as wearables, are small computers worn at the body of an individual and performing health, lifestyle, fitness and/or other functions. To give an example, a wearable can be used to measure the pulse beat of an individual. Smartwatches, fitness bracelets and digital glasses are typical further examples of wearables. Devices for measuring the blood sugar content and/or the blood pressure are further examples of wearables.

In an embodiment, the substrate is a medical device. This medical device might be a non-implantable medical device. In an embodiment, however, the medical device is an implantable medical device. Thereby, it might be intended for a temporal or permanent implantation into the body of a human or animal individual.

In an embodiment, the substrate is a balloon catheter or the expandable part (i.e., the balloon) of a balloon catheter. Then, the expansion of this balloon catheter can be accurately measured by the strain sensor applied to the surface of the balloon catheter. In doing so, it is possible to expand the balloon catheter exactly to a desired size. E.g., the balloon can be expanded such that an over-expansion of a stent surrounding the balloon catheter is achieved so that the stent, after recoiling, properly corresponds to the diameter of the vessel into which the stent is to be implanted. The balloon catheter can also be used for (digitally) measuring the diameter of the vessel into which the balloon catheter is introduced.

In particular in case of the substrate being a medical device such as a balloon catheter, the strain sensor is applied onto an outer surface of the substrate. This facilitates manufacturing of the strain sensor and still guarantees for exact measuring of an expansion or relaxation of the substrate.

In an aspect, the present invention relates to a method for manufacturing an arrangement according to the preceding explanations, i.e., a strain sensor arrangement. This manufacturing method comprises the steps explained in the following.

In a first step, a substrate is provided.

Afterwards, a strain sensor is formed onto the substrate by directly printing an ink composition onto the surface of the substrate. Thereby, the ink composition comprises a mixture of a conductive (and stretchable) silver ink and a conductive (and stretchable) carbon ink. A ratio between the conductive silver ink and the conductive carbon ink lies in a range between 30:70 and 70:30.

In a preferred embodiment, the ratio between the conductive silver ink and the conductive carbon ink lies in a range between 40:60 and 60:40.

Finally, the printed ink composition is dried to obtain on operational strain sensor made from the ink composition.

It is generally possible to apply any appropriate printing technique for printing the strain sensor onto the surface of the substrate. In an embodiment, the printing technique is chosen from the group consisting of inkjet printing, screen printing, pad printing, reel-to-reel printing, flatbed printing and spray printing.

An appropriate printer is a printer for printing hardware such as a printed circuit board (PCB). Such a printer typically makes use of an inkjet printing technique or a spray printing technique. The ink used for printing is kept in a cylinder and pressed through a nozzle. The printing unit is moved on an x-y axis system so that almost any pattern can be precisely printed onto different substrates. The pattern to be printed can be defined by generally available computer programs.

The curing step of the manufacturing method can be a passive curing step or an active curing step. In passive curing step, the printed ink composition is simply left alone without altering the conditions. Then, the ink typically slowly dries due to evaporation of a solvent being present in the ink. When performing the curing step as active curing step, the environmental conditions of the printed ink are altered to achieve a faster curing of the ink.

In an embodiment, the curing is performed at a temperature of at least 80° C., in particular at least 90° C., in particular at least 95° C., in particular at least 100° C., in particular at least 110° C., in particular at least 120° C., in particular at least 130° C., in particular at least 140° C., in particular at least 150° C. In an embodiment, the temperature is chosen from a temperature lying in the range between 90° C. and 160° C. or any other interval that can be built up from the precedingly mentioned temperatures (such as a temperature range of 100° C. to 150° C.). The ink composition is then left at this temperature for a first period of time. This time period is, in an embodiment, a time period lying in a range of 1 minute to 60 minutes, in particular 2 minutes to 50 minutes, in particular 3 minutes to 45 minutes, in particular 4 minutes to 40 minutes, in particular 5 minutes to 35 minutes, in particular 6 minutes to 30 minutes, in particular 10 minutes to 25 minutes, in particular 15 minutes to 20 minutes. If the ink composition is dried at an elevated temperature, curing of the ink composition may occur during this curing step. While some conductive silver inks and some conductive carbon inks requires such a curing, other conductive silver inks and other conductive carbon inks do not require such curing. But even if an ink composition does not require curing, curing can be done at an elevated temperature as indicated above.

In a preferred embodiment where the substrate is a balloon of a balloon catheter, the curing is performed at a temperature between 80° C. and 100° C., in particular between 85° C. and 95° C., in particular at 90° C. In this embodiment the ink is left at these temperatures for a time period in a range between 2 minutes and 30 minutes, in particular between 5 minutes and 10 minutes.

All variants and embodiments explained with respect to the described arrangement can also be applied in an analogous manner to the described method, and vice versa. Thereby, any combination between the variants and embodiments are possible and are herewith disclosed.

FIG. 1 shows a diagram on the change of the electric resistance of a strain sensor made from conductive silver ink (available as DuPont PE873 from DuPont) in dependence on the applied strain. Thereby, the results of three different cycles of expansion and subsequent relaxation are displayed. The continuous curve represents the measured electric resistance upon expansion of the strain sensor; the dashed curves represent the measured electric resistance measured upon relaxation of the same strain sensor.

Under ideal conditions, the continuous curve and the dashed curve of each cycle (i.e., the black continuous curve and the black dashed curve, the grey continuous curve and the grey dashed curve, as well as the black-rimmed grey continuous curve and the black-rimmed grey dashed curve would lie over each other.

As apparent from FIG. 1, only the curves from the first expansion and relaxation cycle are relatively closely to each other. However, the measured resistances in case of the relaxation in the second cycle and the relaxation in the third cycle are significantly lower than the measured resistances of the expansions in the second and third cycle at the same strain. Thus, pure conductive silver ink shows a significant hysteresis with respect to the measured electric resistance as function of the applied strain.

Figure 2:
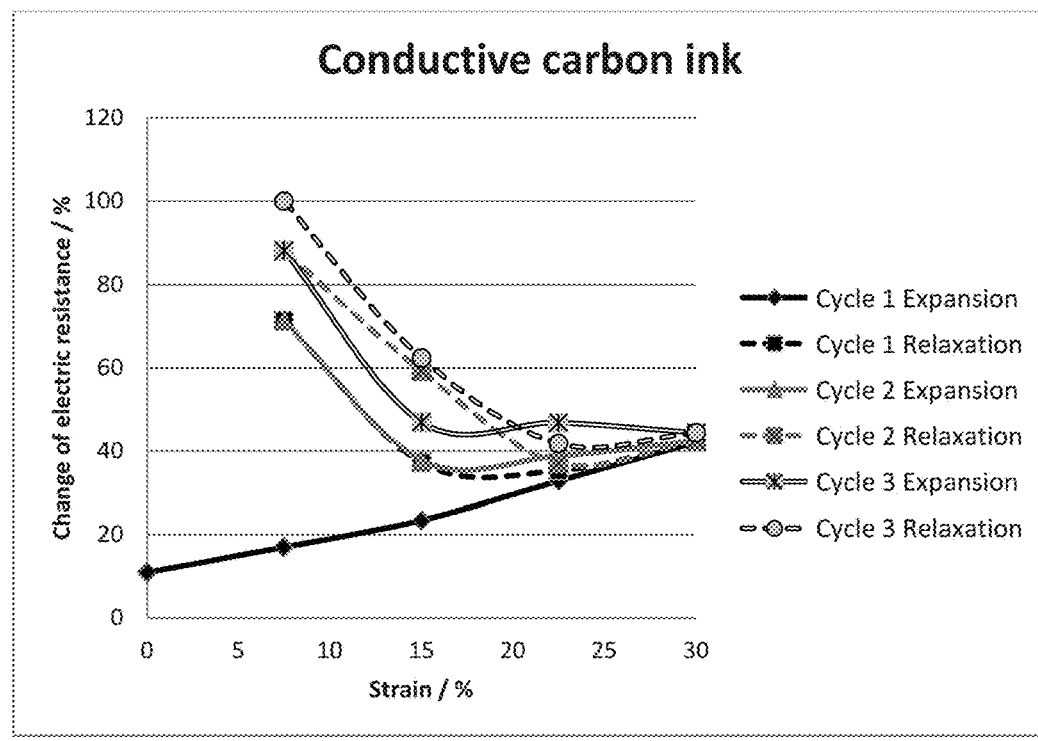
FIG. 2 shows a diagram on the change of the electric resistance of conductive carbon ink in dependence on the applied strain.

The situation is even worse in case of pure conductive carbon ink (available as DuPont Intexar PE671 from DuPont) that shows a completely different behavior of the electric resistance as function of the strain in the first expansion and relaxation cycle, as can be seen from FIG. 2. Additionally, the measured resistance upon relaxation is much higher in the second and third applied expansion and relaxation cycle than in case of the corresponding expansions. Thus, also conductive carbon ink shows significant hysteresis between the measured resistances upon expansion and relaxation.

Figure 3:
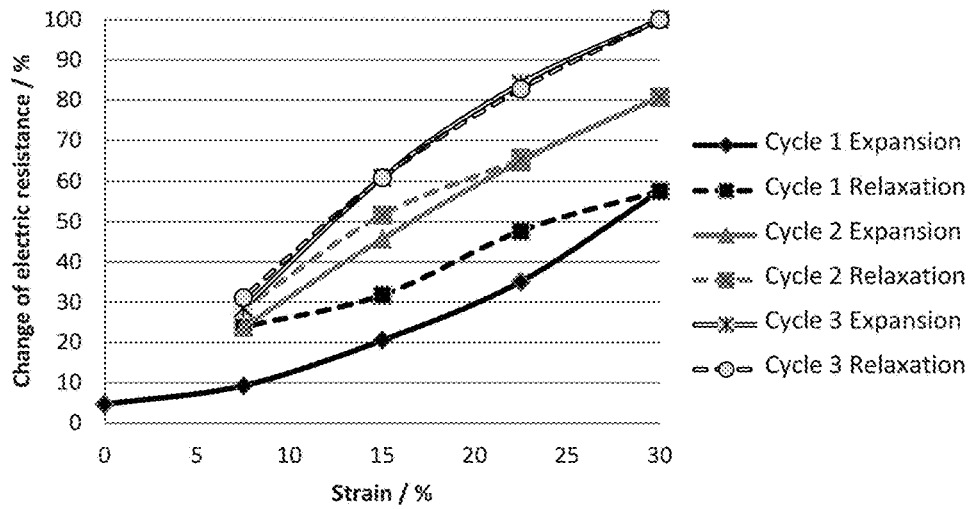
FIG. 3 shows a diagram on the change of the electric resistance of a first hybrid ink in dependence on the applied strain.

FIG. 3 shows the results of an experiment in which a strain sensor made from hybrid ink (a 50:50 mixture of conductive silver ink and conductive carbon ink used in the experiments the results of which are depicted in FIGS. 1 and 2) was used for measuring the dependency between electric resistance and applied strain. While there still is a deviation of the measured electric resistance in the first expansion and relaxation cycle between the results obtained upon expansion and the results obtained upon relaxation, this difference almost vanishes in the second and third expansion and relaxation cycle. Here, the obtained curves closely match each other so that the measuring results do not deviate between measurements performed upon expansion of the substrate onto which the strain sensor was applied and measurements performed upon relaxation of the substrate.

Thus, a 50:50 mixture of conductive silver ink and conductive carbon ink (hybrid ink) shows physical properties that make this ink particularly appropriate for manufacturing a strain sensor from it. Such a strain sensor does not show significant hysteresis between measurements performed upon expansion and measurements performed upon relaxation of the strain sensor.

Figure 4:
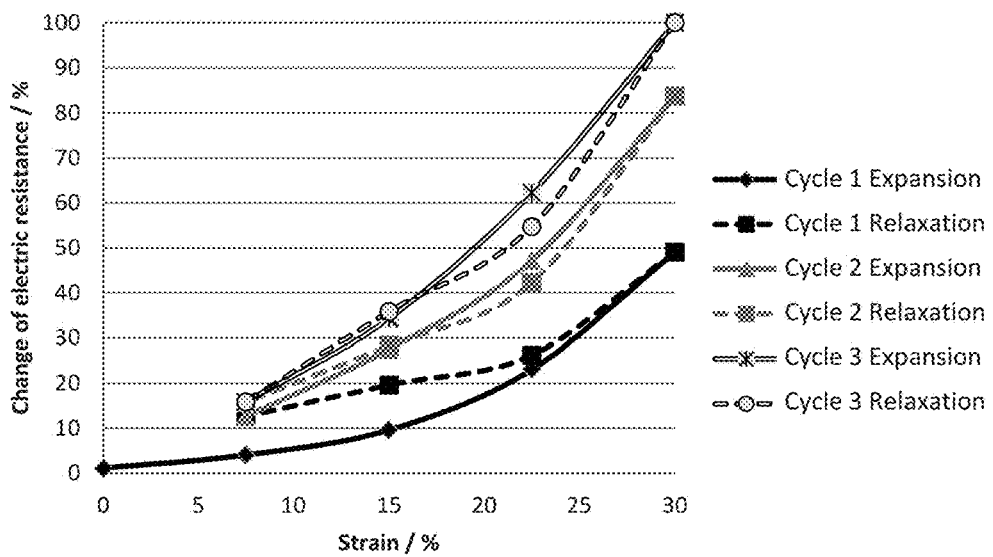
FIG. 4 shows a diagram on the change of the electric resistance of a second hybrid ink in dependence on the applied strain.

Similar results could be obtained when producing a strain sensor from hybrid ink containing conductive silver ink and conductive carbon ink in a ratio of 60:40. Once again, the same inks were used as in the experiments the results of which are depicted in FIGS. 1 and 2. The according results with this hybrid ink are depicted in FIG. 4. Also here, the curves obtained by measuring the electric resistance upon expansion and upon relaxation of the strain sensor closely match each other and do not show a significant hysteresis.

The situation is, however, different in case of other ratios between the same conductive silver ink and the same conductive carbon ink. FIG. 5 shows as comparative example the result obtained with a hybrid ink containing conductive silver ink and conductive carbon ink in a ratio of 75:25. Here, significant deviations between the measured electric resistances as function of the applied strain could be observed upon expansion and relaxation in three consecutive expansion and relaxation cycles.

Likewise, significant differences in the measured electric resistance could be observed in case of a hybrid ink containing the same conductive silver ink and the same conductive carbon ink in a ratio of 25:75. Here, the measured electric resistance upon relaxation of the strain sensor made from this hybrid ink showed in each of the three consecutive expansion and relaxation cycles a significantly different behavior than the electric resistance measured upon expansion of the strain sensor. These results are depicted in FIG. 6.

Thus, hybrid inks containing conductive silver ink and conductive carbon ink in a ratio of 75:25 or 25:75 are not quite appropriate for manufacturing strain sensors having a low hysteresis.

Figure 7:
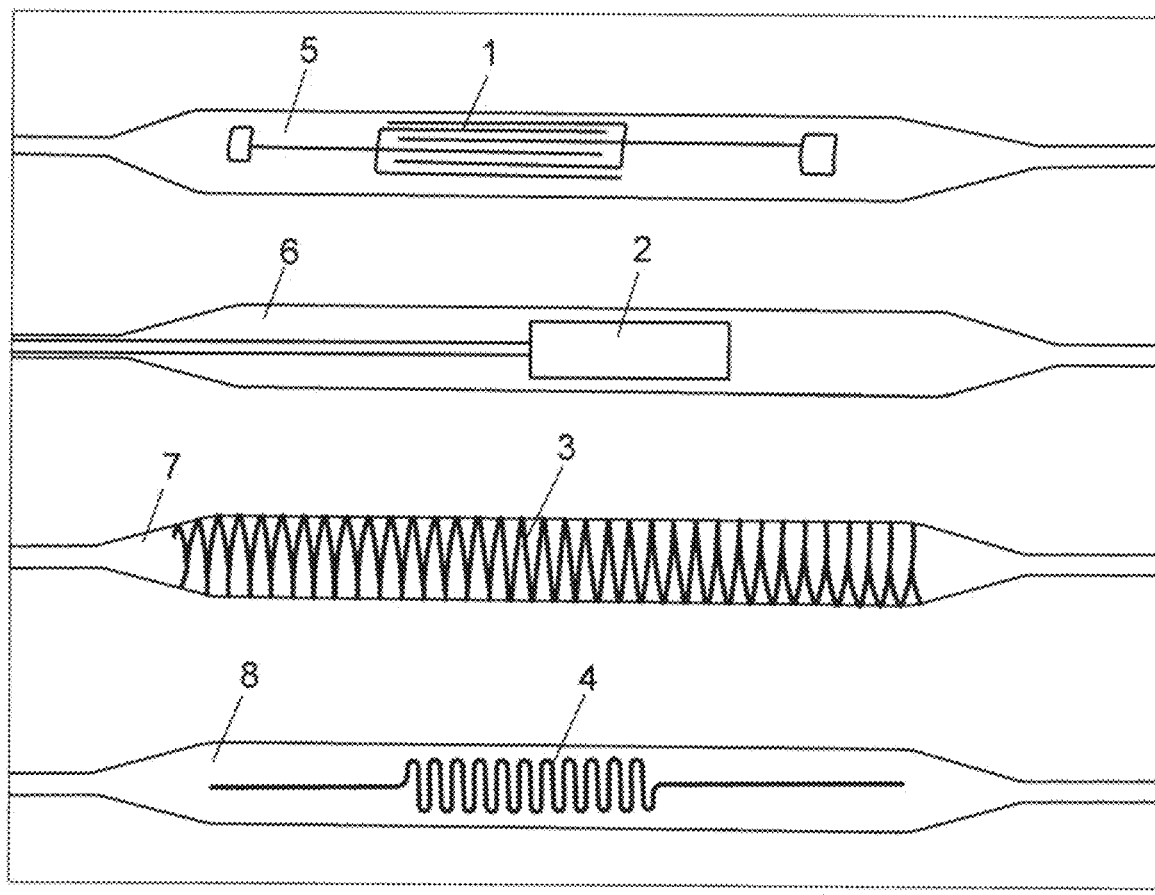
FIG. 7 shows four exemplary embodiments of strain sensors printed onto the outer surface of a balloon catheter.

FIG. 7 shows four different exemplary embodiments of strain sensors 1, 2, 3, 4 applied to the outer surface of a balloon catheter 5, 6, 7, 8. Thereby, the strain sensors 1, 2, 3, 4 are made from a hybrid ink of conductive silver ink and conductive carbon ink mixed in a ratio of 50:50.

The topmost panel of FIG. 7 shows a strain sensor 1 in form of an interdigital capacitor. The second panel from the top shows a strain sensor 2 in form of a cylinder capacitor. The third panel from the top shows a strain sensor 3 in the form of a coil. The lowest panel of FIG. 7 shows a resistive strain sensor 4. All different types of strain sensors 1, 2, 3, 4 measure the strain applied to them (or to the balloon catheters 5, 6, 7, 8 onto which the strain sensors 1, 2, 3, 4 are applied) on basically the same principle. Upon application of a strain, the electrical properties of the strain sensors 1, 2, 3, 4 change. By applying a voltage to the strain sensors 1, 2, 3, 4, the strain acting on the strain sensors 1, 2, 3, 4 can be calculated from the measured electric properties (i.e., from a measured electric resistance or a measured current).

The invention claimed is:

1. Arrangement comprising an expandable or elastic substrate and a strain sensor applied onto a surface of the substrate, wherein the strain sensor comprises an ink composition mixture of a conductive silver ink and a conductive carbon ink, wherein a ratio between the conductive silver ink and the conductive carbon ink lies in a range between 30:70 and 70:30, wherein the ink composition is printed in the form of an interdigitated capacitor, a cylindrical capacitor, a coil, or a resistive strain sensor such that strain transmitted from the expandable or elastic substrate changes an electrical property of the ink composition that can be measured by application of voltage to the ink composition.

2. The arrangement according to claim 1, wherein the ratio between the conductive silver ink and the conductive carbon ink is in a range between 40:60 and 60:40.

3. The arrangement according to claim 2, wherein the ratio between the conductive silver ink and the conductive carbon ink is 50:50.

4. The arrangement according to claim 1, wherein the ink composition comprises a solids content between 40% and 55% determined at 150° C.

5. The arrangement according to claim 1, wherein the strain sensor has a thickness lying in a range between 5 and 200 μm.

6. The arrangement according to claim 1, wherein the substrate is a wearable computer.

7. The arrangement according to claim 1, wherein the substrate is a medical device.

8. The arrangement according to claim 1, wherein the substrate is an implantable medical device.

9. The arrangement according to claim 1, wherein the substrate is a balloon catheter.

10. The arrangement according to claim 1, wherein the strain sensor is applied onto an outer surface of the substrate.

11. The arrangement according to claim 1, wherein the ink composition mixture consists of the conductive silver ink and the conductive carbon ink.

12. The arrangement according to claim 1, wherein the expandable or elastic substrate comprises an elastic substrate.

13. The arrangement according to claim 1, wherein the expandable or elastic substrate comprises a polymeric material.

14. The arrangement according to claim 1, wherein the expandable or elastic substrate comprises a thickness between 1 μm and 20 mm.

* * * * *